United States Patent [19]

Ong et al.

[11] Patent Number: 4,845,263
[45] Date of Patent: Jul. 4, 1989

[54] LAYERED PHOTORESPONSIVE IMAGING MEMBERS WITH SULFUR INCORPORATED DICYANOMETHYLENEFLUORENE CARBOXYLATE COMPOSITIONS OF MATTER

[75] Inventors: Beng S. Ong; Dasarao K. Murti, both of Mississauga, Canada

[73] Assignee: Xerox Corporation, Stamford, Conn.

[21] Appl. No.: 764,049

[22] Filed: Aug. 9, 1985

Related U.S. Application Data

[62] Division of Ser. No. 669,499, Nov. 8, 1984, Pat. No. 4,546,059.

[51] Int. Cl.$^4$ .......................................... C07C 119/02
[52] U.S. Cl. .................................................... 558/427
[58] Field of Search .......................................... 558/427

[56] References Cited

U.S. PATENT DOCUMENTS 3,637,798  1/1972  Sulzberg ............................. 558/427
4,161,490  7/1979  Turner ................................ 558/427
4,546,059  10/1985  Ong et al. ............................ 430/59

Primary Examiner—Alan Siegel

[57] ABSTRACT

Disclosed are photoresponsive imaging members comprised of sulfur incorporated dicyanomethylenefluorene carboxylate electron transporting compounds of the formula:

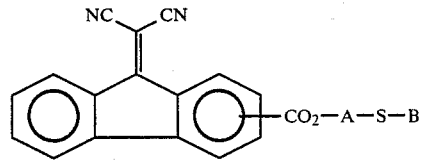

wherein S is sulfur, A is a spacer group selected from the group consisting of alkylene groups, arylene groups, substituted alkylene groups, and substituted arylene groups, and B is selected from the group consisting of alkyl groups, aryl groups, substituted alkyl groups, and substituted aryl groups.

15 Claims, 1 Drawing Sheet

LAYERED PHOTORESPONSIVE IMAGING MEMBERS WITH SULFUR INCORPORATED DICYANOMETHYLENEFLUORENE CARBOXYLATE COMPOSITIONS OF MATTER

This is a division of application Ser. No. 669,499, filed Nov. 8, 1984, now U.S. Pat. No. 4,546,059.

BACKGROUND OF THE INVENTION

This invention is generally directed to layered photoresponsive imaging members comprised of novel electron transporting compounds and more specifically, the present invention is directed to sulfur incorporated dicyanomethylenefluorene carboxylates which can be selected for use in layered photoresponsive imaging members as electron transporting substances. Accordingly, in one specific embodiment of the present invention there is provided a layered photoresponsive imaging member, or device with a photogenerating layer, and in contact therewith an electron transporting substance comprised of sulfur incorporated dicyanomethylenefluorene carboxylates dispersed in an inactive resinous binder material. In one alternative embodiment of the present invention there is provided a layered photoresponsive device wherein the electron transporting compositions selected have added thereto, or are doped with various effective stabilizers, inclusive of aromatic diamines as illustrated herein. Imaging members having incorporated therein the novel organic sulfur compositions of the present invention as electron transporting substances are useful in many imaging systems, particularly electrostatographic imaging systems wherein the member is initially charged positively, thereby enabling the use of such a member for generating colored images and wherein known negatively charged developer compositions can be selected, thereby desirably, in some instances, eliminating the need for charge enhancing additives.

The use of electron transporting substances in photoresponsive imaging members is disclosed in a copending application U.S. Ser. No. 521,198, entitled Layered Photoresponsive Device, the disclosure of which is totally incorporated herein by reference. In this application, there is described an improved photoresponsive imaging member comprised of a supporting substrate, a photogenerating layer, and in contact with the photogenerating layer, an electron transporting layer comprised of novel fluorenylidenemethane compositions. While these compositions are suitable for the intended purposes, there is a need for other electron transporting materials especially those which are relatively stable in resinous binders, and thus do not crystallize; and further wherein the resulting imaging member has improved cycle-up, an cycle-down characteristics.

Also, the formation and development of electrostatic latent images on the imaging surfaces of photoconductive materials by electrostatic means is well known. The photoreceptor selected is generally comprised of a conductive substrate containing on its surface a layer of photoconductive material, and in many instances a thin barrier layer is situated between the substrate and the photoconductive layer to prevent charge injection from the substrate, which injection could adversely affect the quality of the images generated.

Numerous different xerographic photoconductive members are known including, for example, a homogeneous layer of a single material, such as vitreous selenium, or a composite layered device with a dispersion of a photoconductive composition. An example of one type of composite xerographic photoconductive member is described, for example, in U.S. Pat. No. 3,121,006 wherein there is disclosed finely divided particles of a photoconductive inorganic compound dispersed in an electrically insulating organic resinous binder. In a commercial form the binder layer comprises particles of zinc oxide uniformly dispersed in a resinous binder, and coated on a paper backing. The binder material as disclosed in this patent comprises a composition which is incapable of transporting for any significant distance injected charge carriers generated by the photoconductive particles. Illustrative examples of specific binder materials include, for example, polycarbonate resins, polyester resins, polyamide resins, and the like.

There are also known photoreceptor compositions comprised of inorganic or organic materials wherein the charge carrier generation and charge carrier transport functions are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the copying apparatus in order to increase performance standards, and to obtain high quality color images. Additionally, layered pohotoresponsive devices are desired which can be charged positively, and contain therin an electron transporting material.

Recently, there have been disclosed layered photoresponsive members comprised of photogenerating layers, and transport layers, as described in U.S. Pat. No. 4,265,990, and overcoated photoresponsive materials with a hole injecting layer, in contact with a transport layer, an overcoating of a photogenerating layer, and a top coating of an insulating organic resin, reference, for example, U.S. Pat. No. 4,251,612. Examples of generating layers disclosed in these patents include trigonal selenium, and phthalocyanines, while examples of transport layers that may be used, which layers transport positive charges, in contrast to the transport layers of the present invention, which transport electrons include certain diamines dispersed in a resinous binder. The disclosure of each of these patents, namely U.S. Pat. Nos. 4,265,990 and 4,251,612, are totally incorporated herein by reference.

Many other patents are in existence describing photoresponsive imaging members including those with photogenerating substances, such as U.S. Pat. No. 3,041,167, which discloses an overcoated imaging member comprised of a conductive substrate, a photoconductive layer, and an overcoating layer of an electrically insulating polymeric material. This member is utilized in electrophotographic copying by, for example, initially charging the member with electrostatic charges of a first polarity, and imaginewise exposing to form an electrostatic latent image, which can be subsequently developed to form a visible image. Prior to each succeeding imaging cycle, the imaging member can be charged with an electrostatic charge of a second polarity which is opposite in polarity to the first polarity. Sufficient additional charges of the second polarity are applied creating across the member a net electrical field of the second polarity. Simultaneously, mobile charges of the first polarity are created in the photoconductive layer by applying an electrical potential to the conductive substrate. The imaging potential which is developed to form the visible image is present across the photoconductive layer, and the overcoating layer.

Furthermore, there is disclosed in U.S. Pat. No. 4,135,928 electrophotographic light sensitive members with 7-nitro-2-aza-9-fluorenylidene-malononitrile as a charge transporting substance. According to the disclosure of this patent, the electrophotographic light sensitive members comprise an electroconductive support, a layer thereof comprising a charge generating substance, and 7-nitro-2-aza-9-fluorenylidene-malononitrile, of the formula, for example, as illustrated in column 1.

Other representative patents disclosing layered photoresponsive imaging members include U.S. Pat. Nos. 4,115,116, 4,047,949, and 4,315,981. There is disclosed in U.S. Pat. No. 4,315,981 patent an electrophotographic recording member with an organic double layer. According to the disclosure of this patent, the recording member consists of an electroconductive support material and a photoconductive layer of organic materials which contain a charge carrier producing dyestuff layer of a compound having an aromatic or heterocyclic polynuclear quinone ring system, and a transparent top layer of certain oxdiazoles. Apparently, this recording member is useful in electrophotographic copying processes where negative charging of the top layer occurs when an electron donor compound is selected for the member involved.

Many of the photoresponsive devices described, such as those disclosed in U.S. Pat. No. 4,265,990, include a transport layer, the function of which is to transport positive charges generated by the photogenerating layer. In a typical imaging sequence, these devices are charged negatively thus necessitating the need for a charge carrier transport material which will allow the migration of positive charges. Similar devices with electron transporting layers are relatively unknown except as disclosed herein particularly with reference to the copending application mentioned.

While photoresponsive imaging members with specific electron transporting layers are described in the referred to copending application which are suitable for their intended purposes, there continues to be a need for improved imaging members, particularly layered members comprised of novel electron transporting materials. Additionally, there continues to be a need for novel electron transporting materials which when selected for layered imaging devices allow the generation of acceptable images, and wherein these devices can be repeatedly used for many imaging cycles without deterioration thereof from the machine environment or surrounding conditions. Moreover, there continues to be a need for improved layered imaging members with electron transporting substances, wherein the materials selected for the respective layers are substantially inert to users of such devices. Further, there continues to be a need for improved layered imaging members comprising electron transporting substances of sulfur incorporated dicyanomethylenefluorene carboxylates, and wherein the resulting imaging members can be positively charged enabling their use, for example, in xerographic color imaging processes with negatively charged toners. Furthermore, there is a need for electron transporting compounds which enable improved cycle-up and cycle-down characteristics when incorporated into photoconductive imaging members, and wherein the resulting members generate less undesirable ozone in comparison to those imaging members which are negatively charged. Additionally, there continues to be a need for positively charged layered photoresponsive imaging members with electron transporting compounds which are inert and safe to the operational users. Moreover, there continues to be a need for improved photoresponsive imaging members which can be prepared with a minimum number of processing steps, and wherein the layers are sufficiently adhered to one another enabling the continuous use of these members in repetitive imaging and printing systems, including color imaging systems.

SUMMARY OF THE INVENTION

It is therefore an object of the present invention to provide novel organic sulfur compounds which are useful as electron transporting substances in photoresponsive imaging members.

It is yet another object of the present invention to provide novel sulfur incorporated dicyanomethylenefluorene carboxylate compositions for incorporation into improved photoresponsive imaging members as electron transporting substances.

A further object of the present invention resides in the provision of improved photoresponsive devices with a photogenerating layer, and an electron transport layer in contact therewith, comprised of the novel sulfur compositions of the present invention.

In a further object of the present invention there are provided processes for the preparation of the novel sulfur incorporated dicyanomethylenefluorene carboxylate compositions illustrated.

In yet another object of the present invention there is provided a layered photoresponsive imaging member comprised of a photogenerating layer and in contact therewith electron transporting compounds of sulfur incorporated dicyanomethylenefluorene carboxylates dispersed in an inactive resinous binder composition.

In a still further object of the present invention there are provided layered photoresponsive imaging members which can be positively charged enabling their use, for example, in xerographic imaging systems wherein color images are generated with negatively charged color toners.

Furthermore, in another object of the present invention there is provided photoresponsive imaging members comprised of a photogenerating layer, and in contact therewith an electron transporting layer comprised of sulfur incorporated dicyanomethylenefluorene carboxylates, which imaging members generate less undesirable ozone in comparison to similar members which are positively charged.

In still a further object of the present invention there are provided layered photoresponsive devices containing an electron transport layer comprised of novel sulf-incorporated dicyanomethylenefluorene carboxylate dispersed in an inactive resinous binder which are safe to the operational users.

Another object of the present invention is to provide layered photoresponsive imaging members with sulfur-incorporated dicyanomethylenefluorene carboxylates, which members are relatively insensitive to the effect of humidity.

These and other objects of the present invention are accomplished by the provision of photoresponsive imaging members comprised of novel electron transporting layers of sulfur-incorporated dicyanomethylenefluorene carboxylates of the following formula:

where S is a sulfur atom, A is a space linkage selected from the group consisting of alkylene groups, arylene groups, substituted alkylene groups, and substituted arylene groups; and B is an alkyl group, an aryl group, a substituted alkyl group, or a substituted aryl group. Additionally, the A-S-B segment can be comprised of a cyclic moiety including, for example, thiophenemethyl, dibenzothiophenemethyl, thienylethyl, thianaphthenemethyl, thiochromyl and the like.

Illustrative examples of alkylene groups include those of from 1 to about 20 carbon atoms, and preferably from 1 to about 8 carbon atoms, such as methylene, ethylene, propylene, butylene, pentylene, hexylene, octylene, and the like. Specific preferred alkylene groups include methylene, ethylene, propylene and butylene. Illustrative alkyl substituents include those of from 1 to about 20 carbon atoms, and preferably from 1 to about 8 carbon atoms, such as for example, methyl, ethyl, propyl, butyl, pentyl, and the like. Arylene and aryl groups can be selected from those of from about 6 to about 24 carbon atoms such as phenylene, phenyl, naphthylene, naphthyl, and the like. These groups can be substituted with various components providing the objectives of the present invention are achieved, inclusive of alkyl and aryl as defined herein, halogen, alkoxy, alkylthio, cyano, and other similar substituents.

Examples of specific novel organic sulfur compositions encompassed within the above general formula, and useful as electron transporting compositions for incorporation into photoresponsive imaging members, include those compounds as respresented by the following formulas:

I

2-METHYLTHIOETHYL
9-DICYANOMETHYLENEFLUORENE-4-CARBOXYLATE

II 2-(3-THIENYL)ETHYL
9-DICYANOMETHYLENEFLUORENE-4-CARBOXYLATE

III

2-PHENYLTHIOETHYL
9-DICYANOMETHYLENEFLUORENE-4-CARBOXYLATE

IV

2-THIOPHENEMETHYL
9-DICYANOMETHYLENEFLUORENE-4-CARBOXYLATE

V p-METHYLTHIOPHENETHYL
9-DICYANOMETHYLENEFLUORENE-4-CARBOXYLATE

VI

2-DIBENZOTHIOPHENEMETHYL
9-DICYANOMETHYLENEFLUORENE-4-CARBOXYLATE

4-THIANOPHTHENEMETHYL

9-DICYANOMETHYLENEFLUORENE-4-CARBOXYLATE

4-THIOCHROMYL

9-DICYANOMETHYLENEFLUORENE-4-CARBOXYLATE

2,2-BIS(METHYLTHIO)PROPYL

9-DICYANOMETHYLENEFLUORENE-4-CARBOXYLATE

The electron transporting compounds described herein are generally prepared by the reaction, at an effective temperature, of (chloroformyl-9-fluorenylidene)malononitrile with a sulfur-incorporated hydroxy compound, in the presence of a suitable base, inclusive of trialkylamine or pyridine. More specifically, in one embodiment there is reacted 1 equivalent of (chloroformyl-9-fluorenylidene)malononitrile with from 1 to 3 equivalents of a sulfur-incorporated hydroxy compound, in the presence of 3 or more equivalents of trialkylamine. The reaction is generally accomplished in a suitable solvent such as methylene chloride or tetrahydrofuran, and at a temperature that will enable the formation of the desired product without undue complication. Usually this temperature is from 0° to about 100° C., and preferably from about 15° to 30° C. The resulting products can be identified by usual analytical tools, inclusive of NMR, IR Mass spectrometry, and elemental analysis.

In one specific embodiment, the reaction is executed in accordance with the following equation:

wherein A, S, and B are as defined herein.

Illustrative examples of sulfur incorporated hydroxy compounds, or alcohols, selected as reactants, include 2-methylthioethanol, 2-phenylthioethanol, p-methylthiobenzyl alcohol, 2-(3-thienyl)-ethanol, 2-thiophenemethanol, 2-dibenzothiophenemethanol, 4-thianaphthenemethanol, 4-thiochromanol, 2,2-bis(methylthio)propanol, and the like, with 2-methylthioethanol, 2-(3-thienyl)ethanol, 2-phenylthioethanol, p-methylthiobenzyl alcohol being preferred. Illustrative examples of trialkylamine reactants are triethylamine, tripropylamine, 1,4-diazabicyclo [2.2.2] octane, diethylpropylamine, N,N,N',N'-tetramethyl-1,4-butanediamine and the like.

Figure 2:
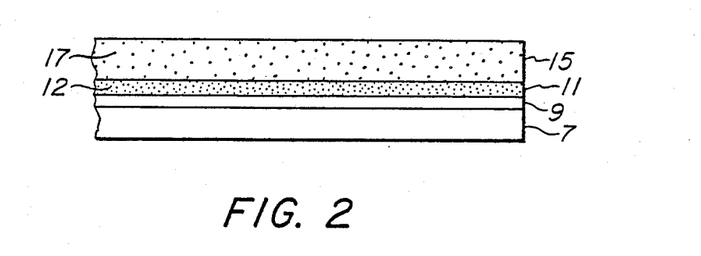
Figure 3:
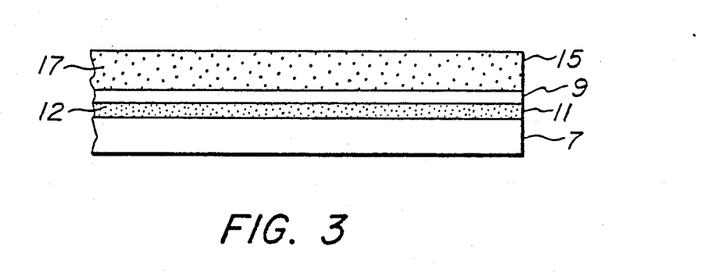

Photoresponsive imaging members comprising the novel electron transporting compositions of the present invention are illustrated with reference to FIGS. 1, 2 and 3.

Figure 1:
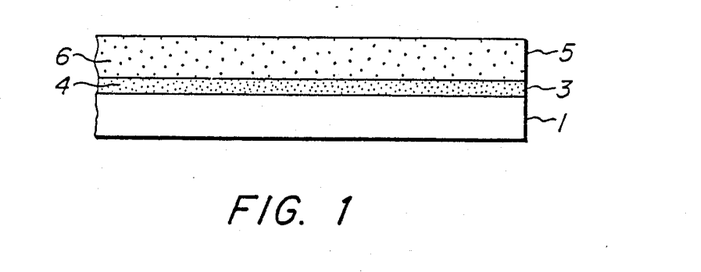

More specifically, there is illustrated in FIG. 1 a photoresponsive imaging member comprised of a supporting substrate 1, a photogenerating layer 3, optionally dispersed in an inactive resinous binder 4, and an electron transporting layer 5, comprised of the electron transporting compositions of the present invention, optionally dispersed in a resinous binder 6. Similarly, there is illustrated in FIG. 2 a photoresponsive imaging member comprised of a supporting substrate 7, an injection barrier layer 9, a photogenerating layer 11, with photogenerating pigments optionally dispersed in an inactive resinous binder 12, and an electron transporting layer 15, comprised of the electron transporting compounds of the present invention, optionally dispersed in a resinous binder 17. Illustrated in FIG. 3 is a further modified photoresponsive device of the present invention substantially equivalent to the photoresponsive device described with regard to FIG. 2, with the exception that the injection barrier layer 9, is situated between the photogenerating layer 11, and the electron transport layer 15.

The photoresponsive imaging members disclosed are useful in electrostatographic imaging processes, particularly colored electrostatic processes, wherein the members are initially charged positively, followed by imagewise exposure, development of the resulting latent image with a developer composition, comprised of toner resin particles, and carrier particles, followed by transferring the developed image to a suitable substrate, such as paper, and permanently affixing the image thereon.

With further reference to the photoresponsive members, the substrate layers are of a thickness of from about 1 mil to about 50 mils, and may be comprised of any suitable material having the requisite mechanical properties. Thus, the substrate layers may comprise a layer of conductive inorganic or metallized organic polymeric material, or a conductive material such as, for example, aluminum, chromium, nickel, brass, or the like. The substrate may be flexible or rigid, and may be of a number of many different configurations, inclusive of, for example, a plate, a cylindrical drum, a scroll, an endless flexible belt, and the like. Preferably, the substrate is in the form of an endless flexible belt.

The photogenerating layers can be comprised of known photoconductive charge carrier generating materials including, for example, amorphous selenium, amorphous selenium alloys, halogen-doped amorphous selenium, halogen-doped amorphous selenium alloys, trigonal selenium, selenide and carbonates with trigonal selenium, reference U.S. Pat. No. 4,232,102 and 4,233,283, the disclosures of each of these patents being totally incorporated herein by reference, cadmium sulfide, cadmium selenide, cadmium telluride, cadmium sulfur selenide, cadmium sulfur telluride, cadmium seleno telluride, copper and chlorine-doped cadmium sulfide, and the like. Alloys of selenium included within the scope of the present invention are selenium tellurium alloys, selenium arsenic alloys, selenium tellurium arsenic alloys, and preferably such alloys with a halogen material, such as chlorine, in an amount of from about 50 to about 500 parts per million.

Other photogenerating pigments are metal phthalocyanines, metal-free phthalocyanines, vanadyl phthalocyanines, other known phthalocyanines, some of which are illustrated in U.S. Pat. No. 3,816,118 the disclosure of which is totally incorporated herein by reference, squarylium pigments, and the like. Preferred photogenerating pigments are trigonal selenium, squarylium compounds, and vanadyl phthalocyanine.

The photogenerating layers are generally of a thickness of from about 0.05 microns to about 10 microns or more, and preferably are of a thickness of from about 0.4 microns to about 3 microns; however, the thickness of this layer is primarily dependent on the photoconductive weight loading, which may vary from 5 to 100 weight percent.

The photogenerating layer comprises the above-described photogenerating pigments optionally dispersed in an inactive resinous binder composition, in amounts of from about 5 percent by weight to about 95 percent by weight, and preferably in amounts of from about 25 percent by weight to about 75 percent by weight. Illustrative examples of polymeric binder resinous materials that can be selected include those as disclosed, for example, in U.S. Pat. No. 3,121,006, the disclosure of which is totally incorporated herein by reference, polyesters, polyvinylbutyal, polycarbonate resins, polyvinylcarbazole, epoxy resins, phenoxy resins, especially the commercially available poly(hydroxyether) resins, and the like.

The electron transporting layer is of a thickness of from about 2 microns to about 100 microns, and preferably is of a thickness of from 5 microns to about 30 microns.

Also, the electron transporting compounds are generally dispersed in a highly insulating and transparent resinous material or inactive resinous binder, including those binders as described in U.S. Pat. No. 3,121,006 the disclosure of which is totally incorporated herein by reference. Specific examples of resinous materials are polycarbonates, acrylate polymers, vinylpolymers, cellulose polymers, polyesters, polysiloxanes, polyamides, polyurethanes, and epoxies, as well as block, random or alternating copolymers thereof. Preferred electrically inactive binder materials are polycarbonate resins with a molecular weight of from about 20,000 to about 100,000 with a molecular weight in the range of from about 50,000 to about 100,000 being particularly preferred. Generally, the resinous binder is present in the electron transporting layer in an amount of from about 25 percent by weight to about 90 percent by weight, and preferably in an amount of from about 50 percent by weight to about 65 percent by weight. Other inactive resinous binder materials can be selected for the electron transporting layer providing the objectives of the present inventinon are achieved, including, for example, polyhydroxy ethers, such as those commercially available from Union Carbide, and the like.

Moreover, the electron transporting compounds of the present invention are easily purified, and further, these compounds desirably do not form, or form in some instances only very weak charge transfer complexes with donor molecules. Additionally, the electron transporting compositions of the present invention are non-mutagenic, and are substantially desirably transparent to visible light.

Additionally, the aforementioned electron transport layers may be doped with certain electron donor molecules to enhance performance or long-term structural stability. Generally, these donors are present in an amount of from about 1 weight percent to 50 weight percnet, and preferably in an amount of from 5 to 25 weight percent. Illustrative examples of suitable electron donor molecules are N-ethylcarbazole, N-isopropylcarbazole, N-phenylcarbazole, N,N-dimethylaniline, triphenylamine, substituted N,N,N',N'-tetraphenyl-1,1'-biphenyl-4,4'-diamines, N-methyl-N,N-diphenylamine, and the like.

Illustrative examples of injection barrier layers useful for the photoresponsive members of the present invention include polysiloxanes, poly(vinylpyrrolidones), polyamides, polyurethanes, polyesters, nitrocellulose, poly(vinylidene chlorides), and the like, with poly(vinylpyrrolidones) and polysiloxanes being preferred. This layer is of a thickness of from about 0.05 microns to about 2 microns.

Toners and developer compositions that may be selected for image development with the photoconductive members of the present invention are well known, and include, for example, compositions comprised of toner resins; pigment particles inclusive of cyan, magenta, and yellow pigments; and carrier particles, reference copending application U.S. Pat. No. 4,537,848, entitled Positively Charged Toner Compositions Containing Phosphonium Charge Enhancing Additives; and U.S. Pat. No. 4,312,932, which also illustrates a color development process. The disclosure of each of these documents is totally incorporated herein by reference. Specific examples of resin particles are styrene methacrylates, styrene acrylates, styrene butadiene, polyesters, and other similar polymers.

The invention will now be described in detail with respect to specific preferred embodiments thereof, it being udnerstood that these examples are intended to be illustrative only and the invention is not intended to be limited to the materials, conditions or process parameters recited herein. All percentages and parts are by weight unless otherwise indicated.

EXAMPLE I

Synthesis of 2-methylthioethyl 9-dicyanomethylenefluorene-4-carboxylate (I)

(a) Preparation of precursor (4-carboxy-9-florenylidene)malononitrile: A mixture of 93.1 grams (0.415 mole) of fluorenone-4-carboxylic acid and 750 milliliters of absolute methanol was magnetically stirred and heated to reflux temperature in a 2,000 milliliter round-bottomed flask fitted with a reflux condenser. Subsequently, there was added to the flask 82.3 grams (1.25 mole) of malononitrile and 20 drops of piperidine. This mixture was then heated under reflux for 48 hours. The solid product (4-carboxy-9-fluorenylidene)-malononitrile, was collected by suction filtration, and purified by stirring in 500 milliliters of boiling methanol for 15 minutes, followed by filtration and washing successively with 200 milliliters of methanol. The product was dried under vacuum at 65° C. for 12 hours and weighed 90.1 grams.

(b) Preparation of (4-chloroformyl-9-fluorenylidene)-malononitrile: A mixture of 27.44 grams (0.10 mole) of (4-carboxy-9-fluorenylidene)malononitrile as obtained in (a) above, and 150 milliliters of thionyl chloride in a 250 milliliter round-bottomed flask equipped with a reflux condenser was magnetically stirred and heated under reflux in a dry nitrogen atmosphere for 6 hours. The solid acid dissolved after 1 hour's heating. As the reaction proceeded, the reaction mixture turned brownish in color, and was a dark brown at the end of the reaction. The reaction mixture was then evaporated at reduced pressure resulting in a solid residue. Thereafter, 300 milliliters of dichloroethane was added to the mixture to dissolve the crude product. The resulting solution was then evaporated under reduced pressure to remove traces of thionyl chloride. The crude product was recrystallized from methylene chloride/hexane (350 ml/400 ml), and the pure (4-chloroformyl-9-fluorenylidene)-malononitrile obtained weighted 27.99 grams after drying under a vacuum at 40° C. for 12 hours.

(c) Preparation of Compound (I): A mixtrue of 10 grams (0.0344 mole) of (4-chloroformyl-9-fluorenylidene)malononitrile prepared in (b) above, and 3.81 grams (0.0413 mole) of 2-methylthioethanol was dissolved in 150 milliliters of dried methylene chloride in a 250 milliliter round-bottomed flask under a dry nitrogen atmosphere. The solution was magnetically stirred at room temperature, and 6 milliliters of triethylamine was added to the solution over a peiod of 5 minutes. After addition, the reaction mixture was allowed to react for another 40 minutes with constant stirring. Subsequently, 100 milliliters of methylene chloride was added, and the reaction mixture was poured into a 500 milliliter separatory funnel, washed once with dilute aqueous hydrochloric acid solution twice with a dilute aqueous sodium bicarbonate solution dried with magnesium sulfate and filtered. The filtrate was concentrated to a final volume of 75 milliliters, followed by dilution with 100 milliliters of methanol. The resulting solution was then treated with 1 gram of Norit with slight heating for 5 minutes and filtered. The filtrate was evaporated to dryness, and the residue was recrystallized from acetonemethanol yielding 9.5 grams of pure product with a melting point of 107°–108 ° C.

Analytical calculation for $C_{20}H_{14}N_2O_2S$: C, 69.35; H, 4.07; N, 8.09. Found: C, 69.47; H, 4.12; N, 8.21.

NMR ($CD_2Cl_2$), delta: 2.15(s, 3H); 2.90(t, 2H); 4.55(t, 2H); 7.1–8.7(m, 7H).

IR (KBr pellet): 2240 cm$^{-1}$(CN); 1735 cm$^{-1}$(C=O).

EXAMPLE II

A layered photoresponsive imaging member containing Compound (I) as synthesized in Example I in a polycarbonate binder as the electron transport layer, and trigonal selenium as the pohtogenerator, was prepared as follows:

A dispersion of trigonal selenium and poly(N-vinylcarbazole) was prepared by ball milling 1.6 grams of trigonal selenium and 1.6 grams of poly(N-vinylcarbazole) in 14 milliliters each of tetrahydrofuran and toluene. Ten grams of the resulting slurry was diluted with a solution of 0.24 grams of N,N'-diphenyl-N,N'bis(3-methylphenyl)-[1,1'-biphenyl]-4,4'-diamine in 5 milliliters each of tetrahydrofuran and toluene. A 1.5 micron thick photogenerator layer was fabricated by coating the above dispersion onto an aluminized Mylar substrate, thickness of 20 mils, with a Bird Film applicator. The coating was dried in a forced air oven at 135° C. for 5 minutes. A solution for the electron transport layer was then prepared by dissolving 1.0 grams of electron transport Compound (I), 0.25 gram of N,N'-diphenyl-N,N'-bis(3-methylphenyl)-[1,1'-biphenyl]-4,4'-diamine and 1.0 gram of Makrolon polycarbonate in 14 milliliters of methylene chloride. This solution was coated over the photogenerator layer by means of a Bird Film applicator. The resulting member was then dried in a forced air oven at 130° C. for 30 minutes, resulting in an 18 micron thick transport layer.

The fabricated imaging member was then electrically tested as follows:

The member was charged positively with a corona, and discharged by exposing to white ligth of wavelengths of 400–700 nanometers. Charging was accomplished with a single wire corotron in which the wire was contained in a grounded aluminum channel and was strung between two insulating blocks. The acceptance potential of this imaging member after charging, and its residual potential after exposure were recorded. The procedure was repeated for different exposure energies, supplied by a 75 Watt Xenon arc lamp of incident radiation, and the exposure energy required to discharge the surface potential of the member to half of its original value was determined. This surface potential was measured using a wire loop probe, contained in a shielded cylinder and placed direclty above the photoreceptor member surface. This loop was capacitively coupled to the photoreceptor surface so that the voltage of the wire loop corresponds to the surface potential. Also, the cylinder enclosing the wire loop was connected to the ground.

For this imaging member the acceptance potential was 1000 volts, the residual potential was 100 volts, and the half decay exposure sensitivity was 12 ergs/cm$^2$.

Further, the electrical properties of this photoreceptor member were essentially the same after 1,000 cycles of repeated charging and discharging.

Specifically, the electrical stability of the photoreceptor member was tested by monitoring the surface potentials for 1,000 cycles. Xerographic cycling is essentially the repetition of a photoinduced dishcarge experiment for a specific number of cycles. Each photoinduced discharge experiment constitutes a single cycle, and typically an individual cycle will include a charging, a dark decay period, exposure, a discharge period, and erasure by light of the remaining charge on the photoreceptor surface.

Electrostatic latent images can thus be generated on the photoconductive member of this Example, reference the $E_{1/2}$ value of 12 ergs/cm$^2$.

EXAMPLE III

A layered photoresponsive imaging member comprised of Compound (I) in Merlon polycarbonate as the electron transport layer, and a trigonal selenium generator layer was fabricated as follows:

A 2 micron thick trigonal selenium photogenerator layer was fabricated on an aluminized Mylar by repeating the procedure of Example II. A solution for the transport layer was then prepared by dissolving 10 grams of Compound (I), 4 grams of the diamine of Example II, and 27 grams of Merlon polycarbonate in 300 milliliters of methylene chloride, and 200 milliliters of 1,1,2-trichloroethane. Thereafter, the solution was spray coated on top of the photogenerator layer by means of a commercial spray gun in a spray booth at 20° C. and 35% relative humidity (R.H.). The resulting member was then dried in a forced air oven at 130° C. for 30 minutes, resulting in dry thickness of the transport layer of 7 microns. Subsequently, the imaging member was cooled to room temperature, followed by electrical testing in accordance with the procedure of Example I with substantially similar results. Specifically, this imaging member was positively charged to fields of 85 volts/micron and dishcarged satisfactorily when exposed to white light of wavelengths of 400–700 nm. The half decay exposure energy for this device was 6 ergs/cm$^2$, and the device was repeatedly subjected to charging and discharging without exhibiting cyclic fatigue.

EXAMPLE IV

A layered photoresponsive imaging member comprised of Compound (I) in Vitel PE-100 polyester (Goodyear) as the electron transport layer, and trigonal selenium as the photogenerator was fabricated as follows:

A 2-micron trigonal selenium photogenerator layer was prepared on an aluminized Mylar substrate in accordance with the procedure as described in Example III. The solution for the transport layer was prepared by dissolving 0.35 gram of Compound (I), 0.13 gram of N,N'-diphenyl-N,N'-bis(3-methylphenyl)-1,1'-biphenyl-4,4'-diamine, and 0.31 gram of Vitel PE-100 polyester in 5 milliliters of methylene chloride. This solution was then coated by means of a Bird Film applicator over the photogenerator layer. Thereafter, the resulting member was dried in a forced air oven at 135° C. for 30 minutes, yielding a transport layer of a thickness of 12 microns.

Electrical testing was affected by repeating the procedure of Example II, and substantially similar results were achieved. The half decay exposure sensitivity for the member of this Example was 9 ergs/cm$^2$.

EXAMPLE V

A layered photoresponsive device comprised of Compound (I) as obtained in Example I, as the transport layer, and amorphous selenium as the photogenerator, was fabricated as follows:

A 1 micron thick layer of amorphous selenium on a ball grained aluminum plate of thickness of 7 mils was prepared by conventional vacuum deposition techniques. Vacuum deposition was accomplished at a vacuum of 10$^{-6}$ torr, while the substrate was maintained at about 50° C. An electron transport layer on top of the amorphous selenium layer was obtained by coating a solution of 50% by weight each of Compound (I) and poly(N-vinylcarbazole) in methylene chloride using a Bird Film applicator. This solution was prepared by dissolving 5 grams of Compound (I), and 5 grams of poly(N-carbazole) in 70 grams of methylene. Thereafter, the resulting device was dried in a forced air oven at 50° C. for 12 hours to form a 10 micron thick transport layer.

Electrical testing was affected by repeating the procedure of Example II, and substantially similar results were achieved. The half decay exposure sensitivity for the member of this Example was 9 ergs/cm$^2$. Specifically, for example, the device was subsequently tested by charging positively to fields of 48 volts/micron and discharging using 400–700 nm white light. The half decay exposure sensitivity for the imaging member of this Example was 65 ergs/cm$^2$.

EXAMPLE VI

Synthesis of 2-(3-thienyl)ethyl 9-dicyanomethylenefluorene-4-carboxylate (II)

The preparation of Compound (II) was accomplished by essentially repeating the procedure of Example I, with the exception that 2-(3-thienyl)ethanol was selected instead of 2-methylthioethanol. In addition, there was a slight difference in the work-up procedure as detailed below:

The filtrate obtained after washing and drying was concentrated to a final volume of 100 milliliters, and was diluted with 100 milliliters of isopropanol. The resulting solution was then treated with 1 gram of Norit with slight heating for 5 minuts and filtered. The filtrate was evaporated to dryness, and the residue was recrystallized from methylene chloride/isopropanol yielding 11.2 grams of pure product with a melting point of 117°–118.5° C.

Analytical Calculation for $C_{23}H_{14}N_2O_2S$: C, 72.25; H, 3.69; N, 7.32. Found: C, 72.18; H, 3.73; N, 7.35.

NMR ($CD_2Cl_2$), delta 3.15(t, 2H); 4.6(t, 2H); 7.0–8.6(m, 10H).

IR (KBr pellet): 2240 cm$^{-1}$(CN); 1735 cm$^{-1}$(C=O).

EXAMPLE VII

A photoresponsive device comprised of Compound (II) as the transport compound, and squarylium pigments as the photogenerator was prepared as follows:

A ball grained aluminum substrate was coated with a solution of 1 milliliter of 3-aminopropyltrimethoxysilane in 100 milliliters of ethanol. The coating was heated at 110° C. for 10 minutes, resulting in the formation of a 0.1 micron thick polysiloxane layer. A dispersion of a photogenerator prepared by ball milling a mixture of 0.075 gram of bis(N,N-dimethylaminophenyl)squaraine and 0.13 gram of Vitel PE-200 polyester (Goodyear) in 12 milliliters of methylene chloride for 24 hours was coated on top of the polysiloxane layer. After drying the coating in a forced air oven at 135° C. for 6 minutes, a 0.5 micron thick squarylium photogenerating layer was obtained.

A solution for the transport layer was then prepared by dissolving 1.0 gram of Compound (II), prepared in accordance with Example VI, 0.3 gram of N-isopropylcarbazole, and 1.0 gram of Makrolon polycarbonate in 20 milliliters of methylene chloride. This solution was then coated over the above photogenerator layer using a Bird Film applicator. The resulting device was dried in a forced air oven at 135° C. for 30 minutes, resulting in a 10 micron thick transport layer.

Electrical testing was affected by repeating the procedure of Example II, and substantially similar results were achieved. The half decay exposure sensitivity for the member of this Example was 9 ergs/cm$^2$. Specifically, this device was charged positively to fields of 65 volts/micron and discharged with 830 nm monochromatic light. Also, the half decay exposure sensitivity for this imaging member was 10 ergs/cm$^2$.

EXAMPLE VIII

A photoresponsive imaging device with a spray coated transport layer comprised of Compound (II), and a trigonal selenium photogenerator was fabricated as follows:

A 2 micron thick trigonal selenium photogenerator layer on an aluminized Mylar was prepared in accordance with the procedure of Example II. A solution for the transport layer was then prepared by dissolving 12 grams of Compound (II), 4 grams of N,N'-diphenyl-N,N'-bis(ethylphenyl)-[1,1'-biphenyl]-4,4'diamine, and 25 grams of Merlon polycarbonate in 200 milliliters of methylene chloride and 300 milliliters of 1,1,2-trichloroethane. This solution was spray coated over the photogenerator layer using a commercial spray gun in accordance with the procedure as described in Example III. The coating was dried in a forced air oven at 135° C. for 30 minutes yielding a transport layer of a thickness of 6 microns.

Electrical testing was affected by repeating the procedure of Example II, and substantially similar results were achieved. The half decay exposure sensitivity for the member of this Example was 9 ergs/cm$^2$. This device could be charging positively to fields of 85 volts/micron, and discharged with 400–700 nm of white light. Also, the half decay exposure sensitivity of this imaging member was 7 ergs/cm$^2$.

EXAMPLE IX

A layered photoresponsive imaging member employing Compound (II) as the transport molecule and vanadyl phthalocyanine as the generator was fabricated as follows:

A 1 micron thick generator layer was coated on a polysiloxanecoated aluminized Mylar in accordance with the procedure of Example VII using vanadyl phthalocyanine instead of squarylium pigment. The polysiloxane layer was of a thickness of 0.05 micron. A transport layer solution identical to that of Example VII was coated over the above photogenerator layer. The device was dried in a forced air oven at 135° C. for 30 minutes, yielding a transport layer of a thickness of 22 microns.

Electrical testing was affected by repeating the procedure of Example II, and substantially similar results were achieved. The half decay exposure sensitivity of this imaging member to 400–700 nm white light was 20 ergs/cm$^2$.

EXAMPLE X

Synthesis of 2-phenylthioethyl 9-dicyanomethylenefluorene-4-carboxylate (III):

The preparation of Compound (III) was accomplished by repeating the procedure of Example VI, with the exception that 1-phenylthioethanol was used instead of 2-(3-thienyl)ethanol. The yield of the pure product, III, was 11.7 grams. Thus, Compound (III) had a melting point of 121°–122° C.

Analytical calculation for $C_{25}H_{16}N_2O_2S$: C, 7351; H, 3.95; N, 6.86, Found: C, 73.60; H.398; n. 675, NMR (CD$_2$Cl$_2$), delta: 3.35(t,2H); 4.6(t,2H); 7.2–8.7(m,12H), IR (KBr pellet): 2240 cm$^{-1}$(CH); 1740 cm$^{-1}$(C=O).

EXAMPLE XI

A layered photoresponsive device comprised of Compound (III) as the electron transport layer, and vanadyl phthalocyanine as the generator was fabricated as follows:

A 1 micron thick vanadyl phthalocyanine generator layer was prepared on a polysiloxane-coated aluminized Mylar in accordance with the procedure of Example IX. A solution for the transport layer was prepared by dissolving 1.0 gram of Compound (III), 1.0 gram of Makrolon polycarbonate, and 0.35 gram of triphenylamine in 20 milliliters of methylene chloride. This solution was coated over the generator layer by means of a Bird Film applicator. The coating was dried in the forced air oven as before, yielding a transport layer of thickness of 18 microns.

Electrical testing was affected by repeating the procedure of Example II, and specifically, for example, with white light (400–700 nm) exposure, a half decay exposure sensitivity of 15 ergs/cm$^2$ resulted for this imaging member. The same sensitivity was obtained when 830 nm monochromatic light was used for exposure.

EXAMPLE XII

A layered photoresponsive imaging member comprised of electron transporting Compound (III) and trigonal selenium photogenerator was fabricated as follows:

A 2 micron thick trigonal selenium generator layer was prepared on a ball grained aluminum plate in accordance with the procedure of Example II. A 9 micron thick transport layer similar to that of Example III using Compound (III) instead of Compound (I) was fabricated by spray coating techniques over the trigonal selenium generator layer. The half decay exposure sensitivity of this device was 10 ergs/cm$^2$.

Although the invention has been described with reference to specific preferred embodiments, it is not intended to be limited thereto but rather those skilled in the art will recognize that variations and modifications may be made therein which are within the spirit of the invention and within the scope of the following claims.

We claim:

1. Sulfur incorporated dicyanomethylenefluorene carboxylate compounds of the formula wherein S in sulfur, A is a spacer group selected from the group consisting of alkylene groups, arylene groups, substituted alkylene groups, and substituted arylene groups, and B is selected from the group consisting of alkyl groups, aryl groups, substituted alkyl groups, and substituted aryl groups.

2. Compounds in accordance with claim 1 wherein A is an alkylene group of from 1 to about 20 carbon atoms.

3. Compounds in accordance with claim 1 wherein A is an alkylene groups of from 1 to about 6 carbon atoms.

4. Compounds in accordance with claim 1 wherein A is methylene or ethylene.

5. Compounds in accordance with claim 1 wherein A is an aryl group of from 6 to about 24 carbon atoms.

6. Compounds in accordance with claim 1 wherein A is phenylene.

7. Compounds in accordance with claim 1 wherein B is an alkyl group of from 1 to about 20 carbon atoms.

8. Compounds in accordance with claim 1 wherein B is an alkyl group of from 1 to about 6 carbon atoms.

9. Compounds in accordance with claim 1 wherein B is methyl or ethyl.

10. Compounds in accordance with claim 1 wherein B is an aryl group of from 6 to about 24 carbon atoms.

11. Compounds in accordance with claim 1 wherein B is phenyl.

12. The compound 2-methylthioethyl 9-dicyanomethylenefluorene-4-carboxylate of the following formula:

13. The compound 2-phenylthioethyl 9-dicyanomethylenefluorene-4-carboxylate.

14. Compounds in accordance with claim 1 wherein the substituted substituents are independently selected from the group consisting of alkyl, aryl, halogen, alkoxy, alkylthio, and cyano.

15. Compounds in accordance with claim 14 wherein alkyl is from 1 to about 20 carbon atoms.

* * * * *